US008460680B2

United States Patent
Chow et al.

(10) Patent No.: US 8,460,680 B2
(45) Date of Patent: Jun. 11, 2013

(54) POLYVALENT CHIMERIC RUBELLA VIRUS-BASED VACCINES

(75) Inventors: Yen-Hung Chow, Miaoli County (TW); Charles Dwo-Yuan Sia, Ontario (CA); Pele Choi-Sing Chong, Miaoli County (TW); Kuang-Nan Hsiao, Miaoli County (TW)

(73) Assignee: National Health Research Institutes, Miaoli County (TW)

( * ) Notice: Subject to any disclaimer, the term of this patent is extended or adjusted under 35 U.S.C. 154(b) by 420 days.

(21) Appl. No.: 12/763,801

(22) Filed: Apr. 20, 2010

(65) Prior Publication Data

US 2010/0272747 A1 Oct. 28, 2010

Related U.S. Application Data

(60) Provisional application No. 61/172,687, filed on Apr. 24, 2009.

(51) Int. Cl.
A61K 39/20 (2006.01)
A61K 39/12 (2006.01)
A61K 39/295 (2006.01)
A61K 39/155 (2006.01)

(52) U.S. Cl.
USPC .......... 424/219.1; 424/218.1; 424/204.1; 424/202.1; 424/211.1

(58) Field of Classification Search
None
See application file for complete search history.

(56) References Cited

U.S. PATENT DOCUMENTS

| 3,686,394 | A | 8/1972 | Huygelen et al. |
| 5,880,104 | A | 3/1999 | Li et al. |
| 6,180,758 | B1 | 1/2001 | Chong et al. |
| 6,958,237 | B2 * | 10/2005 | Frey et al. ............... 435/320.1 |
| 7,118,888 | B2 | 10/2006 | Mohapatra et al. |

OTHER PUBLICATIONS

Tang, et al. Parainfluenza virus type 3 expressing the native or soluble fusion (F) Protein of Respiratory Syncytial Virus (RSV) confers protection from RSV infection in African green monkeys. J Virol. 2004; 78(20): 11198-11207.*
Manicassamy, et al. Comprehensive Analysis of Ebola Virus GP1 in Viral Entry. J. Virol. 2005; 79(8):4793-4805.*
Wertz et al. "Expression of the fusion protein of human respiratory syncytial virus from recombinant vaccinia virus vectors and protection of vaccinated mice" J Virol. Feb. 1987; 61(2): 293-301.

* cited by examiner

Primary Examiner — Zachariah Lucas
Assistant Examiner — Stuart W Snyder
(74) Attorney, Agent, or Firm — Hsiu-Ming Saunders; Intellectual Property Connections, Inc.

(57) ABSTRACT

A chimeric viral particle that comprises a RV fusion gene is disclosed. The RV fusion gene comprises a first nucleotide sequence encoding a RV that is devoid of RV E1 protein, and a second nucleotide sequence that linked in translation frame to the first nucleotide sequence and encodes a humoral immunogenic viral protein. The chimeric viral particle is free of RV E1 protein-encoding gene. A virus packaging cell that generates the chimeric viral particle comprising a RV fusion gene and an isolated expression vector comprising a RV fusion gene linked in translation frame to a promoter are also disclosed.

20 Claims, 6 Drawing Sheets

FIG. 1A pRVwt: NS-ORF — Junction UTR — SP-ORF (C, E2, E1)

FIG. 1B pΔE1RV

FIG. 1C pΔE1RV-GFP — GFP

FIG. 1D pΔE1RV-RSV F0 — RSV F0

FIG. 1E pΔE1RV-RSV F0 — RSV F0ΔTM

FIG. 1F pΔE1RV-hPIV-3 HN-RSV F0 — hPIV-3 HN — RSV F0

FIG. 1G pΔE1RV-hPIV-3 HN — hPIV-3 HN

SEQUENCE LISTING

```
<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: Forward primer for the target gene RV E1

<400> SEQUENCE: 1
aggctttcac ctacctctgc                                              20

<210> SEQ ID NO 2
<211> LENGTH: 19
<212> TYPE: DNA
<213> ORGANISM: Artificial Sequence
<220> FEATURE:
<223> OTHER INFORMATION: Reverse Primer for the target gene RV E1

<400> SEQUENCE: 2
cgccagggtt gaagtaaga                                               19

<210> SEQ ID NO 3
<211> LENGTH: 19
<212> TYPE: DNA
<213> ORGANISM: Artificial Sequence
<220> FEATURE:
<223> OTHER INFORMATION: Forward primer for the target gene RV E2

<400> SEQUENCE: 3
cgccagggtt gaagtaaga                                               19

<210> SEQ ID NO 4
<211> LENGTH: 20
<212> TYPE: DNA
<213> ORGANISM: Artificial Sequence
<220> FEATURE:
<223> OTHER INFORMATION: Reverse primer for the target gene RV E2

<400> SEQUENCE: 4
atagcgcagc caaaccgggt                                              20

<210> SEQ ID NO 5
<211> LENGTH: 25
<212> TYPE: DNA
<213> ORGANISM: Artificial Sequence
<220> FEATURE:
```

<223> OTHER INFORMATION: Forward primer for the target gene RV C

<400> SEQUENCE: 5
gcttctacta cccccatcac catgg    25

<210> SEQ ID NO 6
<211> LENGTH: 20
<212> TYPE: DNA
<213> ORGANISM: Artificial Sequence
<220> FEATURE:
<223> OTHER INFORMATION: Reverse primer for the target gene RV C

<400> SEQUENCE: 6
taaaagaccg cgccttcgcc    20

<210> SEQ ID NO 7
<211> LENGTH: 24
<212> TYPE: DNA
<213> ORGANISM: Artificial Sequence
<220> FEATURE:
<223> OTHER INFORMATION: Forward primer for the target gene RV NS

<400> SEQUENCE: 7
atggagagac tcctagatga ggtt    24

<210> SEQ ID NO 8
<211> LENGTH: 23
<212> TYPE: DNA
<213> ORGANISM: Artificial Sequence
<220> FEATURE:
<223> OTHER INFORMATION: Reverse primer for the target gene RV NS

<400> SEQUENCE: 8
acatctgcat gggtgtgtag tag    23

<210> SEQ ID NO 9
<211> LENGTH: 20
<212> TYPE: DNA
<213> ORGANISM: Artificial Sequence
<220> FEATURE:
<223> OTHER INFORMATION: Forward primer for the target gene RSV F

<400> SEQUENCE: 9
tggagctgcc catcctgaag    20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for the target gene RSV F

<400> SEQUENCE: 10
tggactgcat cagcagctgc    20

<210> SEQ ID NO 11
<211> LENGTH: 22
<212> TYPE: DNA
<213> ORGANISM: Artificial Sequence
<220> FEATURE:
<223> OTHER INFORMATION: Forward primer for the target gene GFP

<400> SEQUENCE: 11
tgagcaaggg cgaggagctg tt    22

<210> SEQ ID NO 12

-continued

```
<211> LENGTH: 24
<212> TYPE: DNA
<213> ORGANISM: Artificial Sequence
<220> FEATURE:
<223> OTHER INFORMATION: Reverse primer for the target gene GFP
<400> SEQUENCE: 12
aagatggtgc gctcctggac gtag 24

<210> SEQ ID NO 13
<211> LENGTH: 1830
<212> TYPE: DNA
<213> ORGANISM: respiratory syncytial virus
<400> SEQUENCE: 13
acctataaat acggatcagc caccatggag acagacacac tcctgctatg ggtactgctg 60
ctctgggttc caggttccac tggtgacgga tccatggagc tgcccatcct gaaggctaac 120
gctatcacca ccatcctggc tgctgtgacc ctgtgcttcg cttcctccca gaacatcacc 180
gaggagttct accagtccac ctgctccgct gtgtccaagg gttacctgtc cgctctgcgt 240
accggttggt acacctccgt gatcaccatc gagctgtcca acatcaagga gaacaagtgc 300
aacggtaccg acgctaaggt gaagctgatc aagcaggagc tggacaagta caagaacgct 360
gtgaccgagc tgcagctgct gatgcagtcc acccccgctg ctaacaaccg tgctcgtcgt 420
gagctgcccc gtttcatgaa ctacaccctg aacaacacca agaacaccaa cgtgaccctg 480
tccaagaagc gtaagcgtcg tttcctgggt ttcctgctgg gtgtgggttc cgctatcgct 540
tccggtatcg ctgtgtccaa ggtgctgcac ctggagggtg aggtgaacaa gatcaagtcc 600
gctctgctgt ccaccaacaa ggctgtggtg tccctgtcca acggtgtgtc cgtgctgacc 660
tccaaggtgc tggacctgaa gaactacatc gacaagcagc tgctgcccat cgtgaacaag 720
cagtcctgcc gtatctccaa catcgagacc gtgatcgagt tccagcagaa gaacaaccgt 780
ctgctggaga tcacccgtga gttctccgtg aacgctggtg tgaccacccc cgtgtccacc 840
tacatgctga ccaactccga gctgctgtcc ctgatcaacg acatgcccat caccaacgac 900
cagaagaagc tgatgtccaa caacgtgcag atcgtgcgtc agcagtccta ctccatcatg 960
tccatcatca aggaggaggt gctggcttac gtggtgcagc tgcccctgta cggtgtgatc 1020
gacacccccct gctggaagct gcacacctcc cccctgtgca ccaccaacac caaggagggt 1080
tccaacatct gcctgacccg taccgaccgt ggttggtact gcgacaacgc tggttccgtg 1140
tccttcttcc cccaggctga gacctgcaag gtgcagtcca accgtgtgtt ctgcgacacc 1200
atgaactccc tgaccctgcc ctccgaggtg aacctgtgca acgtggacat cttcaacccc 1260
aagtacgact gcaagatcat gacctccaag accgacgtgt cctcctccgt gatcacctcc 1320
ctgggtgcta tcgtgtcctg ctacggtaag accaagtgca ccgcttccaa caagaaccgt 1380
ggtatcatca agaccttctc caacggttgc gactacgtgt ccaacaaggg tgtggacacc 1440
gtgtccgtgg gtaacaccct gtactacgtg aacaagcagg agggtaagtc cctgtacgtg 1500
aagggtgagc ccatcatcaa cttctacgac cccctggtgt tcccctccga cgagttcgac 1560
gcttccatct cccaggtgaa cgagaagatc aaccagtccc tggctttcat ccgtaagtcc 1620
gacgagctgc tgcacaacgt gaacgctggt aagtccacca ccaacatcat gatcaccacc 1680
atcatcatcg tgatcatcgt gatcctgctg tccctgatcg ctgtgggtct gctgctgtac 1740
tgcaaggctc gttccacccc cgtgaccctg tccaaggacc agctgtccgg tatcaacaac 1800
atcgctttct ccaacgaatt catcgagggt 1830
```

-continued

<210> SEQ ID NO 14
<211> LENGTH: 1620
<212> TYPE: DNA
<213> ORGANISM: Human parainfluenza virus 3

<400> SEQUENCE: 14

```
atgcccacct ccatcctgct gatcatcacc accatgatca tggccagctt ttgccagatc     60
gacatcacca agctgcagca cgtgggcgtg ctggtgaaca gccccaaggg catgaagatc    120
agccagaact tcgagacacg ctacctgatc ctgagcctga tccccaagat cgaggacagc    180
aacagctgcg gcgaccagca gatcaagcag tacaagaagc tgctggaccg gctgatcatc    240
cccctgtacg acggcctgcg gctgcagaaa gacgtgatcg tgaccaacca ggaaagcaac    300
gagaacaccg acccccggac caagagattc ttcggcggcg tgatcggcac aattgccctg    360
ggcgtggcca caagcgccca gattacagcc gccgtggccc tggtggaagc caagcaggcc    420
agaagcgaca tcgagaagct gaaagaggcc atccgggaca ccaacaaggc tgtgcagagc    480
gtgcagtcca gcatcggcaa cctgatcgtg gccatcaagt ccgtgcagga ctacgtgaac    540
aaagaaatcg tgcccagcat tgccagactg ggctgcgaag ccgctggcct gcagctgggc    600
attgctctga cccagcacta cagcgagctg accaacatct tcggcgacaa catcggctca    660
ctgcaggaaa agggcatcaa gctgcagggc attgccagcc tgtaccggac caacatcacc    720
gagatcttca ccacctccac cgtggacaag tacgacatct acgatctgct gttcaccgag    780
agcatcaaag tgcgcgtgat cgacgtggac ctgaacgact acagcatcac actgcaggtc    840
cggctgcctc tgctgacccg gctgctgaac acccagatct acaaggtgga cagcatcagc    900
tacaacatcc agaaccggga gtggtacatc cccctgccca gccacatcat gaccaagggc    960
gcctttctgg gcggagccga cgtgaaagag tgcatcgagg ccttcagcag ctacatctgc   1020
cccagcgacc ccggcttcgt gctgaaccac gagatcgaga gctgcctgag cggcaacatc   1080
agccagtgcc ccagaaccac cgtgaccagc gacatcgtgc cccgctacgc ctttgtgaat   1140
ggcggcgtgg tggccaactg tatcaccacc acctgtacct gtaacggcat cggcaatcgg   1200
atcaaccagc cccccgacca gggcgtgaag attatcaccc acaaagaatg cagcaccgtg   1260
gggatcaacg gcatgctgtt caacaccaac aaagagggca ccctggcctt ctacaccccc   1320
aacgacatca ccctgaacaa cagcgtgacc ctggacccca tcgacatcag catcgagctg   1380
aacaaggcca agagcgacct ggaagagtcc aaagagtgga tccggcggag caaccagaag   1440
ctggactcca tcggcaactg gcaccagagc agcaccacaa tcatcatcat cctgatcatg   1500
atcatcattc tgttcatcat caacatcacc atcatcacaa tcgccatcaa gtactaccgg   1560
atccagaaac ggaaccgggt ggaccagaac gataagccct acgtgctgac caataagtga   1620
```

<210> SEQ ID NO 15
<211> LENGTH: 9759
<212> TYPE: DNA
<213> ORGANISM: Rubella virus

<400> SEQUENCE: 15

```
caatggaagc tatcggacct cgcttaggac tcccattccc atggagaaac tcctagatga     60
ggttcttgcc cccggtgggc cttataactt aaccgtcggc agttgggtaa gagaccacgt    120
ccgctcaatt gtcgagggcg cgtgggaagt gcgcgatgtt gttaccgctg cccaaaagcg    180
ggccatcgta gccgtgatac ccagacctgt gttcacgcag atgcaggtca gtgatcaccc    240
agcactccac gcaatttcgc ggtatacccg ccgccattgg atcgagtggg gccctaaaga    300
```

-continued

```
agccctacac gtcctcatcg acccaagccc gggcctgctc cgcgaggtcg ctcgcgttga   360
gcgccgctgg gtcgcactgt gcctccacag gacggcacgc aaactcgcca ccgccctggc   420
cgagacggcc agcgaggcgt ggcacgctga ctacgtgtgc gcgctgcgtg gcgcaccgag   480
cggccccttc tacgtccacc ccgaggacgt tccgcacggc ggtcgcgccg tggcggacag   540
atgcttgctc tactacacac ccatgcagat gtgcgagctg atgcgcacca ttgacgccac   600
cttgctcgtg gcggttgact tgtggccggt cgcccttgcg gcccacgtcg gcgatgactg   660
ggacgacctg ggcattgcct ggcatctcga ccatgacggc ggttgccccg ccgattgccg   720
tggagccggc gctgggccca cgcccggcta caccccgcccc tgcaccacac gcatctacca   780
agtcctgccg gacaccgccc accccgggcg cctctaccgg tgcgggcccc gcctgtggac   840
gcgcgactgc gccgtggccg aactctcatg ggaggttgcc caacactgcg ggcaccaggc   900
gcgcgtgcgc gccgtgcgat gcaccctccc tatccgccac gtgcgcagcc tccaacccag   960
cgcgcgggtc cgactcccgg accttgtcca tctcgccgag gtgggctggt ggcggtggtt  1020
cagcctcccc cgccccgtgt tccagcgtat gctgtcctac tgcaagaccc tgagcccgga  1080
cgcgtactat agcgagcgcg tgttcaagtt caagaacgcc ctgagccaca gcatcacgct  1140
cgcgggcaat gtgctgcaag aggggtggaa gggcacgtgc gccgaagaag acgcgctgtg  1200
cgcgtacgtg gccttccgcg cgtggcagtc taacgccagg ctggcgggga ttatgaaaag  1260
cgcgaagcgc tgccgcgccg actccttgag cgtggccggc tggctggaca ccatttggga  1320
cgccattaag cggttcttcg gcagcgtgcc cctcgccgag cgcatggagg agtgggaaca  1380
ggacgccgcg gtcgccgcct cgaccgcgg cccccctcgaa gacggcgggc gccacttgga  1440
caccgtgcaa ccccccaaat cgccgccccg ccctgagatc gccgcgacct ggatcgtcca  1500
cgccgccagc gcagaccgcc attgcgcgtg cgcccccccgc tgcgacgtcc cacgcgaacg  1560
tccctccgcg cctgccggcc cgccggatga cgaggcgctt atcccgccgt ggctgttcgc  1620
cgagcgccgt gccctccgct gccgagtg ggatttcgag gctctccgcg cgcgcgccga  1680
tacggcggcc gcgcccgccc cgctggctcc acgccctgcg cggtacccca ccgtgctcta  1740
ccgccacccc gcccaccacg gtccgtggct caccccttgac gagccgggcg gggccgacgc  1800
ggccctggtc ttatgcgacc cacttggcca gccgctccgg ggccctgaac gccactacgc  1860
cgccggcgcg catatgtgcg cgcaggcgcg ggggctccag gctttcgtcc gtgtcgtgcc  1920
tccacccgag cgcccctggg ctgacggggg cgccagagcg tgggcgaagt tcttccgcgg  1980
ctgcgcctgg gcgcagcgct tgctcggcga ccggcagtc atgcacctcc catacaccga  2040
tggcgacgtg ccaaagctga tcgcactggc cttgcgcacg ctggcccaac agggggccgc  2100
cttggcactc tcggtgcgtg acctgccccg gggtacagcg ttcgaggcaa atgcggtcac  2160
cgccgccgtg cgcgctggcc ccggccagct cgcggccacg tcaccgccac ccggcgaccc  2220
cccgccgccg cgccgcgcac ggcgatcgca acgcactcg gacgcccgcg gcactccgcc  2280
ccccgcgcct gtgcgcgacc cgcccccgccc ccagcccagc ccgcccgcgc caccccgcgt  2340
gggtgacccg gtccctccca ctaccgcgga gccggcggat cgcgcgcgtc acgccgagct  2400
ggaggtcgtc tacgaaccga gcggcccccc cacgtcaacc aaggcagacc cagacagcga  2460
catcgttgaa agttacgccc gcgccgcgg acctgtgcac ctccgagtcc gcgacatcat  2520
ggacccaccg cctggctgca aggtcgtggt taacgccgcc aacgaggggt tgctggccgg  2580
ctccggcgtg tgcggtgcga tctttgccaa cgccacggcg gccctcgctg cagactgccg  2640
gcgcctcgcc ccatgcccca tcggcgaggc ggtggcgaca cccggccacg gctgcgggta  2700
```

-continued

| | |
|---|---|
| cacccacatc atccacgccg tcgcaccgcg gcgtcctcgg gaccccgccg ccctcgagga | 2760 |
| gggcgaagcg ctgctcgagc gcgcctaccg cagcatcgtc gcgctagccg ccgcgcgtcg | 2820 |
| gtgggcgcgc gtcgcgtgcc ccctcctcgg cgctggcgtc tacggctggt ctgctgcgga | 2880 |
| gtcccttcga gccgcgctcg cggctacgcg cgccgagccc gccgagcgcg tgagcctgca | 2940 |
| catctgccac cccgaccgcg ccacgctgac gcacgcctcc gtgctcgtcg gtgcggggct | 3000 |
| cgctgccagg cgcgtcagtc ctcctccgac cgagcccctc gcatcttgcc ccgcggtga | 3060 |
| cccgggccga ccggctcagc gcagcgcgtc gcccccagcg accccctcg gggatgccac | 3120 |
| cgcgcccgag ccccgcggct gccaggggtg cgaactctgc cggtacacgc gcgtcaccaa | 3180 |
| tgaccgcgcc tatgtcaact tgtggctcga gcgcgaccgc ggcgccacca gctgggcgat | 3240 |
| gcgcattccc gaggtggttg tctacggtcc ggagcacctc gccacgcact ttccattaaa | 3300 |
| ccactacagt gtgctcaagc ccgcggaggt caggcccccg cgaggcatgt gcgggagtga | 3360 |
| catgtggcgc tgccgcggct ggcagggcat gccgcaggtg cggtgcaccc cctccaacgc | 3420 |
| tcacgccgcc ctgtgccgca caggcgtgcc ccctcgggtg agcacgcgag cggcgagct | 3480 |
| agacccaaac acctgctggc tccgcgcgcg cgccaacgtt gcgcaggctg cgcgcgcctg | 3540 |
| cggcgcctac acgagtgccg ggtgccctaa gtgcgcctac ggccgcgccc tgagcgaagc | 3600 |
| ccgcactcat gaggacttcg ccgcgctgag ccagtggtgg agcgcgagcc acgccgatgc | 3660 |
| ctcccctgac ggcaccggag accccctcga ccccctgatg gagaccgtgg gatgcgcctg | 3720 |
| ttcgcgcgta tgggtcggct ccgagcacga ggccccgccc gaccacctcc tggtgtccct | 3780 |
| ccaccgtgcc cccaatggtc cgtggggcgt agtgctcgag gtgcgcgcgc gccccgaggg | 3840 |
| gggcaaccc accggccact tcgtctgcgc ggtcggcggc ggccacgcc gcgtctcgga | 3900 |
| ccgcccccac ctttggctcg cggtcccct gtctcggggc ggcggcactt gtgccgccac | 3960 |
| cgacgagggg ctggcccagg cgtactacga cgacctcgag gtgcgccgcc tcggggacga | 4020 |
| cgccatggcc cgggcggccc tcgcatcaat ccaacgcccc cgcaaaggcc cctacaatat | 4080 |
| cagggtatgg aacatggccg caggcgctgg caagaccacc cgcatcctcg ctgccttcac | 4140 |
| gcgcgaagac ctctacgtct gccccaccaa tgcgctcctg cacgagatcc aggccaaact | 4200 |
| ccgcgcgcgc gatatcgaca tcaagaacgc cgccacctac gagcgcgcgc tgacgaaacc | 4260 |
| gctcgccgcc taccgccgca tctacatcga tgaggcgttc actctcggcg gcgagtactg | 4320 |
| cgcgttcgtt gccagccaaa ccaccgcgga ggtgatctgc gtcggtgatc gggaccagtg | 4380 |
| cggcccacac tacgccaata actgccgcac cccgtccct gaccgctggc ctaccgggcg | 4440 |
| ctcacgccac acttggcgct tccccgactg ctgggcggcc cgcctgcgcg cggggctcga | 4500 |
| ttatgacatc gagggcgagc gcaccggcac cttcgcctgc aacctttggg acggccgcca | 4560 |
| ggtcgacctt cacctcgcct tctcgcgcga aaccgtgcgc cgccttcacg aggctggcat | 4620 |
| acgcgcatac accgtgcgcg aggcccaggg tatgagcgtc ggcaccgcct gcatccatgt | 4680 |
| aggcagggac ggcacggacg ttgccctggc gctgacacgc gacctcgcca tcgtcagcct | 4740 |
| gacccgggcc tccgacgccc tctacctcca cgagctcgag gacggcttac tgcgcgctgc | 4800 |
| ggggctcagc gcgttcctcg atgccggggc actggcggag ctcaaggagg ttcccgccgg | 4860 |
| cattgaccgc gttgtcgccg tcgagcaggc accaccaccg ttccgcccg ccgacggcat | 4920 |
| ccccgaggcc caagacgtgc cgcccttctg cccccgcact ctagaggagc tcgtcttcgg | 4980 |
| ccgtgcgggc caccccatt acgcggacct caaccgcgtg actgagggcg aacgagaagt | 5040 |
| gcggtatatg cgcatctcgc gtcacctgct caacaagaat cacaccgaga tgcccggaac | 5100 |

```
ggaacgcgtt ctcagtgccg tttcgccgtg cggctaccgc gcgggcgagg atgggtcgac    5160
cctccgcact gctgtggccc gccagcaccc gcgcccttc cgccagatcc cacccccgcg     5220
cgttactgct ggggttgccc aggagtggcg catgacgtac ttgcgggaac ggatcgacct    5280
cactgatgtc tacacgcaga tgggcgtggc cgcgcgggag ctcaccgacc gctacacgcg    5340
ccgctatcct gagatctttg ccggcatgtg caccgcccag agcctgagcg tccccgcctt    5400
cctcaaggcc accttgaagt gcgtagacgc cgccctcggc caagggaca ccgaggactg     5460 ccacgctgct caggggaaag ccggccttga gatccgggca tgggccaagg agtgggttca    5520
ggtcatgtct ccgcatttcc gcgcgatcca aagatyatc atgcgcgccc tgcgcccgca     5580
attccttgtg gccgctggcc atacggagcc cgaggtcgac gcctggtggc aggctcatta    5640
caccaccaac gccatcgagg tcgacttcac tgagttcgac atgaaccaga cccttgctac    5700
tcgggacgtc gagctcgaga tcagcgccgc tctcttgggc ctcccttgcg ccgaagacta    5760
ccgcgcgctc cgccgcggca gctattgcac tctgcgcgaa ctgggctcca ctgagaccgg    5820
ctgcgagcgc acaagcggcg agcccgcyac gctactgcac aacaccaccg tggccatgtg    5880
catggctatg cgcatggtcc ccaaaggcgt gcgctgggcc gggattttcc agggcgacga    5940
tatggtcatc ttcctccccg agggcgcgcg caatgcggca ctcaagtgga cccccgccga    6000
ggtgggcttg ttcggcttcc acatcccagt gaagcatgtg agcaccccaa ccccccagctt    6060 ctgcgggcac gtcggcaccg cggccggcct cttccatgat gtcatgcacc aggcaatcaa    6120
ggtgctttgc cgccgtttcg accccgacgt gcttgaagaa cagcaggtgg ccctcctcga    6180
ccgcctccgg ggggtctacg cggctctgcc tgacaccgtt gccgccaatg ctgcgtacta    6240
tgactacagc gcggagcgcg tcctcgctat cgtgcgcgaa cttaccgcgt acgcgcgggg    6300
gcgcggcctc gaccacccgg ccaccatcgg cgcgctcgag gagattcaga ctccctacgc    6360
gcgcgccaat ctccacgacg ctgactaacg ccccgtacg tgggccttt aatctcatct       6420 actctaacca ggtcatcacc caccgttgtt tcgccgcatc tggtgggtac ccactcttg     6480 ccattcggga gagccccagg gtgcccgaat ggcttccact accccatca ccatggagga     6540 ccttcagaag gccctcgagg cacaatcgcg cgccctgcgc gcgggtctcg ccgccggcgc    6600
ctcgcagtcg cgccggccgc ggcgccgcg acagcgcgac tccagcacct ccggagatga     6660
ctccggccgt gactccggag ggcccgccg ccgccgcgg aaccgggcc gtggccagcg       6720 caaggactgg tccagggccc cgccccccc cgaagagcgg caagaaagtc gctcccagac    6780 tccgccccg aagccatcgc gggcgccgcc acaacagcct caaccccgc gtatgcaaac      6840 cgggcgtggg ggctctgccc cgcgccctga gctggggccg ccgaccaacc cgttccaggc    6900
agccgtggcg cgtggcctgc gcccgcctct ccatgaccct gacaccgagg cacccactga    6960
ggcctgcgtg acctcatggc tttggagcga gggcgaaggc gcggtcttct accgcgtcga    7020
cctgcatttt accaacctgg gcaccccccc actcgacgag gacggccgct gggaccctgc    7080
gctcatgtac aaccctttgcg ggcctgagcc gcccgctcac gtcgtccgcg cgtacaacca    7140
acctgccggc gacgtccggg gcgtatgggg taaaggcgag cgcacctacg ccgagcagga    7200
tttccgcgtc ggcggcacgc gctggcaccg actgctgcgc atgccagtgc gcggcctcga    7260
cggcgacacg gcccgcttc cccctcacac caccgagcgc attgagaccc gctcggcgcg     7320
ccgtccttgg cgcatccgct cggtgcccc ccaggccttc ctcgccgggc tcttgctcgc     7380
cgcggtcgcc gttggcaccg cgcgcgcgg gctccagccc cgcgctgata tggcggcacc    7440
ccctatgccg ccacagcccc cccgtgcgca cgggcagcat tatggtcacc accaccatca    7500
```

```
gctgccgttc ctcgggcacg acggccatca cggcggcacc ttgcgcgtcg ccagcatca     7560 ccgaaacgcc agcgacgtgc tgcccggcca ctggctccaa ggcggctggg gttgctacaa    7620
cctgagcgac tggcaccagg gcactcatgt ctgtcacacc aagcacatgg acttctggtg    7680
tgtggagcac gaccgaccgc cgcccgcgac cccgacgtct ctcaccaccg cggcgaacta    7740
cattgccgcc gccacccccg ccactgcgcc gcccccctgc cacgccggcc tcaatgacag    7800
ctgcggcgga ttcttgtctg ggtgcgggcc gatgcgcctg cgccacgcg ctgacacccg     7860 gtgcggtcgg ttgatctgcg ggctgtccac caccgcccag tacccgccta cccggtttgg    7920
ctgcgccatg cggtggggcc tccccccctg ggaactggtc gttcttaccg cccgccccga    7980
agacggctgg acttgtcgtg gcgtgcccgc ccatccaggt acccgctgcc ccgaactggt    8040
gagccccatg ggacgtgcga cttgctcccc agcctcggcc ctctggctcg ccacagcgaa    8100
cgcgctgtct cttgaccacg cgttcgcggc ctttgtcctg ttggtcccgt gggtcctgat    8160
atttatggtg tgccgccgcg cctgtcgccg ccgcggcgcc gccgccgccc tcaccgcagt    8220
cgtcctgcag gggtacaacc ccccgccta tggcgaggag gctttcacct acctctgcac     8280
tgcaccgggg tgcgccactc aaacacctgt ccccgtgcgc ctcgccggcg tcggcttcga    8340
gtctaagatt gtggacggcg gctgcttttgc cccatgggac ctcgaggcta ctggagcctg   8400
catttgcgag atccccactg atgtttcgtc gagggcttg ggggcctggg tacccacagc     8460
cccttgcgcg cgcatctgga atggcacaca gcgcgcgtgc accttctggg ctgtcaacgc    8520
ctactcctct ggcgggtacg cgcagctggc ctcttacttc aaccctggcg gcagctacta    8580
caagcagtac caccccaccg cgtgcgaggt tgaacctgcc ttcggacaca gcgacgcggc    8640
ctgctggggc ttccccaccg acaccgtgat gagcgtgttc gccctcgcta gctacgtcca    8700
gcaccctcac aagaccgtcc gggtcaagtt tcatacagag actaggaccg tctggcaact    8760
ctccgtagcc ggcgtgtcgt gcaacgtcac cactgaacac ccgttctgca acacgccgca    8820
cggacaactc gaggtccagg tcccgcccga ccctggggac ctggtcgagt acattatgaa    8880
ttacaccgga aaccaacagt cccggtgggg cctcgggagc ccgaattgtc atggccccga    8940
ttgggcctcc ccggtttgcc aacgccattc ccctgactgc tcgcggcttg tgggggccac    9000
gccagagcgt ccccggctgc gcctggtcga cgccgacgac cccctgctgc gcactgcccc    9060
cgggcccggc gaggtgtggg tcacgcctgt cataggctct caggcgcgca agtgcggact    9120
ccacatacgt gctggaccgt acggccatgc taccgtcgaa atgcccgagt ggatccacgc    9180
ccacactacc agcgacccct ggcacccacc gggcccttg gggctgaagt tcaagacagt     9240
tcgcccggtg gccctgccac gcgcgttagc gccacctcgc aatgtgcgtg tgaccggctg    9300
ctaccagtgc ggtaccccg cgctggtgga aggccttgcc ccaggggag ggaactgcca      9360 tcttaccgtc aatggcgagg acgtcggcgc cttccccct gggaagttcg tcaccgccgc     9420
cctcctcaac actcccccgc cctaccaagt cagctgcggg ggtgagagcg atcgcgcgag    9480
cgcgcgggtc attgacccg ccgcgcaatc gtttaccggc gtggtgtatg cacacacac      9540 cactgctgtg tcggagaccc ggcagacctg gcgagtgg ctgctgctc attggtggca       9600 gctcactctg ggcgccattt gcgccctcct actcgctggc ttactcgctt gctgtgccaa    9660
atgcttgtac tacttgcgcg gcgctatagc accgcgctag cgggccccg cgcgaaaccc     9720 gcactagccc actagattcc cgcacctgtt gctgcatag                           9759
```

POLYVALENT CHIMERIC RUBELLA VIRUS-BASED VACCINES

REFERENCE TO RELATED APPLICATION

The present application claims the priority of U.S. Provisional Application Ser. No. 61/172,687 filed Apr. 24, 2009, which is herein incorporated by reference in its entirety.

FIELD OF THE INVENTION

The present invention relates generally to respiratory syncytial virus (RSV) vaccines, and more specifically to vaccines comprising nucleic acid sequences encoding rubella virus (RV) proteins and the fusion (F) protein of RSV.

BACKGROUND OF THE INVENTION

Human respiratory syncytial virus (RSV), a member of the Paramyxovirus subfamily Pneumovirinae, is a negative-sense, single-stranded RNA virus of the family Paramyxoviridae. It is the most common cause of viral lower respiratory tract infections in infants and children, affecting about 4 million children globally and leading to about 100,000 hospitalizations and 4,500 deaths per year in the United States alone. RSV infection is associated with recurrent episodes of bronchiolitis, bronchial obstruction and exacerbation of asthma in children. Incidence of RSV infection-induced bronchiolitis has been increasing (WO 03/028759 A1). There is no effective prophylaxis available against RSV infection. Previous attempts to develop a vaccine using a formalin-inactivated RSV vaccine not only failed but also exacerbated diseases when subsequent RSV infection occurred (Parrott et al. (1969) "respiratory syncytial virus disease in infants despite prior administration of antigenic inactivated vaccine" *Am J Epidemiol* 89:422-34). Thus, development of a RSV vaccine has been a high priority at a global level.

Virus-specific cytotoxic T lymphocytes (CTL) play a major role in the clearance of RSV infection. Both antibodies and MHC-class-I restricted T lymphocytes (CTLs) mediate protections against RSV infection. The envelope proteins F and G antigens induce the majority of the neutralizing antibodies against RSV. RSV-specific CTL play a crucial role in mediating virus clearance. An analysis of the CTL repertoire in humans indicated that the N, SH, F, M, M2, and NS2 proteins are strong target antigens. In BALB/c mice, the F, N, and M2 proteins are shown to be the major target antigens of CTL activity (Domachowske et al, (1999) "Respiratory syncytial virus infection: immune response, immunopathogenesis, and treatment" *Clin Microbiol Rev* 12:298). Among the RSV proteins, the F protein has been found to be the major target antigen that induces anti-viral CTL.

The F protein is made of two subunits, $F_2$ and $F_1$. The $F_2$ subunit dimerizes with $F_1$ subunit to form an inactive precursor fusion protein called $F_0$ (Rixon et al., (2002) "Multiple glycosylated forms of the respiratory syncytial virus fusion protein are expressed in virus-infected cells" *J Gen Virol* 83(Pt 1): 61-6). Host cell specificity of RSV infection of the epithelial cells in the respiratory tract is determined by the N-terminal region of the $F_2$ subunit protein. Binding to the permissive cell targets is enhanced by the attachment of the G protein to glycosaminoglycans on the cell membrane of host cells (Feldman et al., (2000) "The fusion glycoprotein of human respiratory syncytial virus facilitates virus attachment and infectivity via an interaction with cellular heparan sulfate" *J Virol* 74(14): 6442-7; Techaarpornkul et al. (2002) "Respiratory syncytial virus with the fusion protein as its only viral glycoprotein is less dependent on cellular glycosaminoglycans for attachment than complete virus" *Virology* 294 (2): 296-304). Virus entry is suggested to involve the fusion of the $F_1$ subunit with the membrane of the target cell. Zhao et al., 2000 "Structural characterization of the human respiratory syncytial virus fusion protein core" *Proc Natl Acad Sci USA.*, 97(26):14172-7; Barghorn et al., (2000) "Structure, microtubule interactions, and paired helical filament aggregation by tau mutants of frontotemporal dementias" *Biochemistry* 39(38): 11714-21). The F glycoprotein has also been shown to form filamentous structures engaged in syncytium formation that further facilitate virus spread (Gower et al., (2001) "RhoA is activated during respiratory syncytial virus infection" *Virology* 283(2): 188-96).

Currently, passive immunization at a monthly interval with a humanized antibody to the RSV-F antigen is considered the only option available to infants, who are at a high risk for developing RSV infection. This approach is inconvenient, expensive, and only partially effective. Therefore, a previously unaddressed need exists in the art to address the aforementioned deficiencies and inadequacies, especially in connection with development of a safe and effective vaccine against RSV.

SUMMARY OF THE INVENTION

In one aspect, the invention relates to a chimeric viral particle comprising a rubella virus (RV) fusion gene, in which the RV fusion gene comprises: a) a first nucleotide sequence encoding a RV that is devoid of RV E1 protein; and b) a second nucleotide sequence, linked in translation frame to the first nucleotide sequence, encoding respiratory syncytial virus (RSV) F protein, in which the chimeric viral particle is free of RV E1 protein-encoding gene.

In another aspect, the invention relates to a chimeric viral particle comprising a RV fusion gene, in which the RV fusion gene comprises: a) a first nucleotide sequence encoding a RV that is devoid of E1 protein; and b) a second nucleotide sequence, linked in translation frame to the first nucleotide sequence, encoding HN of hPIV-3, in which the chimeric viral particle is free of RV E1 protein-encoding gene.

Further in another aspect, the invention relates to a chimeric viral particle comprising a RV fusion gene, in which the RV fusion gene comprises: a) a first nucleotide sequence encoding a RV that is devoid of RV E1 protein; and b) a second nucleotide sequence, linked in translation frame to the first nucleotide sequence, encoding a humoral immunogenic viral protein, in which the chimeric viral particle is free of RV E1 protein-encoding gene.

Yet in another aspect, the invention relates to an isolated expression vector comprising a RV fusion gene linked in translation frame to a promoter, in which the RV fusion gene comprises: i) a first nucleotide sequence encoding a RV that is devoid of E1 gene; and ii) a second nucleotide sequence, linked in translation frame to the first nucleotide sequence, encoding a humoral immunogenic viral protein, in which the expression vector is devoid of RV E1 protein-encoding nucleotide sequence.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention.

Wherever possible, the same reference numbers are used throughout the drawings to refer to the same or like elements of an embodiment.

BRIEF DESCRIPTION OF THE DRAWINGS

FIGS. 1A-1G show the structural maps of the individual plasmids.

FIG. 3B is a photograph of gel electrophoresis analysis of RT-PCR products.

FIG. 5 is a graph showing antiserum titer.

DETAILED DESCRIPTION OF THE INVENTION

Definitions

Figure 2A:
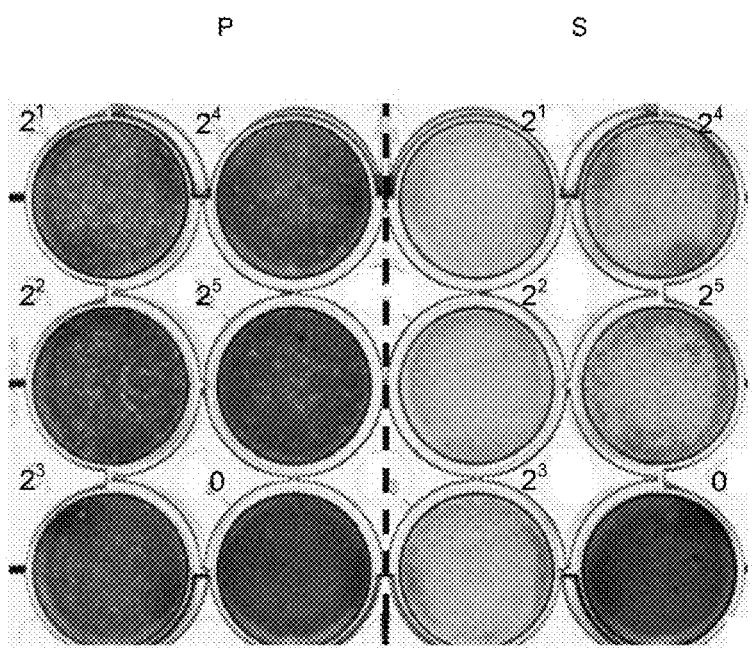
FIG. 2A is a photograph showing a plague assay with BHK-21 cells for evaluation of Vero cells in producing RV.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "attenuated live virus" refers to a rubella virus (RV) strain, the virulence of which has been attenuated.

The term "bivalent" refers to conferring immunity to two diseases or two serotypes bivalent vaccine protecting against two types of viruses.

The terms "multivalent" and "polyvalent" are interchangeable, referring to having more than one valence, having a valence of 3 or higher or acting against or interacting with more than one kind of antigen, antibody, toxin, or microorganism. A multivalent or polyvalent vaccine is a vaccine prepared from several antigenic types An immunization against infections caused by the respiratory syncytium virus (RSV) and parainfluenza type 3 virus (PIV-3) is currently an unmet health care need. The invention employs a regulatory authority approved vaccine strain of rubella virus (RV) expression vector designated RV 27/3 to construct a bivalent recombinant E1-gene deleted RV candidate vaccine that coexpresses respiratory syncytial virus (RSV) fusion (F) gene for immunization against RSV and RV infections. The rationale for making the invention is that RV is a mucosal disease pathogen and that RSV is a leading pathogen that infects epithelial cells of respiratory tract. Mucosal delivery of the recombinant RV 27/3 vaccine candidate is therefore an ideal strategy to induce anti-viral mucosal responses against these pathogens. The capsid (C) protein of RV can induce protective anti-viral IgA antibodies. Anti-C protein-specific humoral responses elicited by the recombinant E1-deleted RV 27/3 and M33 vectors according to the invention can therefore afford protections against RV. The RSV F protein and PIV-3 HN are selected to be incorporated into the E1-deleted RV 27/3 expression vector for the construction of recombinant RV multivalent vaccines.

The invention opens up the opportunities of evaluating the immunogenicity of E1-deleted RV 27/3 and M33 expression vectors in a polyvalent form under a mucosal-subcutaneous vaccination regimen. Preclinical evaluations of the immunogenicity of the multivalent vaccine candidates may be conducted with such an immunization scheme in animals to assay the production of virus-specific mucosal and systemic antibodies as well as the cellular responses generated.

In one aspect, the invention relates to a chimeric viral particle comprising a rubella virus (RV) fusion gene, in which the RV fusion gene comprises: a) a first nucleotide sequence encoding a RV that is devoid of RV E1 protein; and b) a second nucleotide sequence, linked in translation frame to the first nucleotide sequence, encoding respiratory syncytial virus (RSV) F protein, in which the chimeric viral particle is free of RV E1 protein-encoding gene.

The chimeric viral particle is useful for manufacturing a viral vaccine. The viral vaccine comprises a nontoxic, physiologically acceptable carrier and an immunogenic amount of the aforementioned chimeric viral particle. The vial vaccine is used in a method for eliciting a humoral immune response against RV and RSV in a mammal. The method comprises the step of administering to a mammal in need thereof a viral vaccine as aforementioned, thereby eliciting a humoral immune response against RV and RSV in the mammal.

In one embodiment of the invention, the RV fusion gene of the aforementioned chimeric viral particle further comprises a third nucleotide sequence, which links in translation frame to the first or the second nucleotide sequence and encodes hemaagglutinin-neuramindase (HN) of human Parainfluenza Virus Type 3 (hPIV-3). This chimeric viral particle is useful for preparing a viral vaccine. The viral vaccine comprises a nontoxic, physiologically acceptable carrier and an immunogenic amount of the chimeric viral particle. The vial vaccine is useful in a method for eliciting a humoral immune response against RV, RSV and hPIV-3 in a mammal. The method comprises the step of administering to a mammal in need thereof a viral vaccine as aforementioned, thereby eliciting a humoral immune response against RV, RSV and hPIV-3 in the mammal.

In another embodiment of the invention, the first nucleotide sequence of the RV fusion gene comprises: i) a first polynucleotide sequence encoding RV nonstructural protein (NSP); ii) a second polynucleotide sequence encoding RV capsid (C) protein; and iii) a third polynucleotide sequence encoding RV E2 protein.

In another aspect, the invention relates to a viral vaccine that comprises a nontoxic, physiologically acceptable carrier and an immunogenic amount of the aforementioned chimeric viral particle.

In another aspect, the invention relates to a virus packaging cell which generates the aforementioned chimeric viral particle, wherein the virus packaging cell's genome comprises: a) a nucleotide sequence encoding RV structural proteins C, E2 and E1; and b) an expression vector comprising a RV fusion gene linked in translation frame to a promoter, wherein the RV fusion gene comprises: i) a first nucleotide sequence encoding a RV that is devoid of E1 gene; and ii) a second nucleotide sequence, linked in translation frame to the first nucleotide sequence, encoding RSV F protein; in which the expression vector is devoid of RV E1 protein-encoding nucleotide sequence.

In another aspect, the invention relates to a virus packaging cell which generates a chimeric viral particle as aforementioned, in which the virus packaging cell's genome comprises: a) a nucleotide sequence encoding RV structural proteins C, E2 and E1; and b) an expression vector comprising a RV fusion gene linked in translation frame to a promoter, wherein the RV fusion gene comprises: i) a first nucleotide sequence encoding a RV that is devoid of E1 protein; ii) a second nucleotide sequence, linked in translation frame with the first nucleotide sequence, encoding respiratory syncytial virus (RSV) F protein; and iii) a third nucleotide sequence, linked in translation frame to the first or the second nucleotide sequence, encoding hemaagglutinin-neuramindase (HN) of human Parainfluenza Virus Type 3 (hPIV-3), in which the expression vector is devoid of RV E1 protein-encoding nucleotide sequence.

In another aspect, the invention relates to a chimeric viral particle comprising a RV fusion gene, in which the RV fusion gene comprises: a) a first nucleotide sequence encoding a RV that is devoid of E1 protein; and b) a second nucleotide sequence, linked in translation frame to the first nucleotide sequence, encoding HN of hPIV-3, in which the chimeric viral particle is free of RV E1 protein-encoding gene. The RV fusion gene may further comprise a third nucleotide sequence, which links in translation frame to the second nucleotide sequence and encodes RSV F protein. The chimeric viral particle may be incorporated into a vial vaccine. The viral vaccine comprises a nontoxic, physiologically acceptable carrier and an immunogenic amount of a chimeric viral particle as aforementioned.

In another aspect, the invention relates to a chimeric viral particle comprising a RV fusion gene, in which the RV fusion gene comprises: a) a first nucleotide sequence encoding a RV that is devoid of RV E1 protein; and b) a second nucleotide sequence, linked in translation frame to the first nucleotide sequence, encoding a humoral immunogenic viral protein, in which the chimeric viral particle is free of RV E1 protein-encoding gene.

In another aspect, the invention relates to a virus packaging cell which generates the chimeric viral particle as aforementioned.

In one embodiment of the invention, the virus packaging cell's genome comprises: a) a nucleotide sequence encoding RV structural proteins C, E2 and E1; and b) an expression vector comprising a RV fusion gene linked in translation frame to a promoter, wherein the RV fusion gene comprises: i) a first nucleotide sequence encoding a RV that is devoid of E1 protein; and ii) a second nucleotide sequence, linked in translation frame to the first nucleotide sequence, encoding hemaagglutinin-neuramindase (HN) of human Parainfluenza Virus Type 3 (hPIV-3); wherein the expression vector is devoid of RV E1 protein-encoding nucleotide sequence.

In another embodiment of the invention, the virus packaging cell's genome comprises: a) a nucleotide sequence encoding RV structural proteins C, E2 and E1; and b) an expression vector comprising a RV fusion gene linked in translation frame to a promoter, wherein the RV fusion gene comprises: i) a first nucleotide sequence encoding a RV that is devoid of E1 protein; ii) a second nucleotide sequence, linked in translation frame to the first nucleotide sequence, encoding hemaagglutinin-neuramindase (HN) of human Parainfluenza Virus Type 3 (hPIV-3); and iii) a third nucleotide sequence, linked in translation frame to the second nucleotide sequence, encoding RSV F protein, wherein the expression vector is devoid of RV E1 protein-encoding nucleotide sequence.

In one embodiment of the invention, the virus packaging cell's genome comprises: a) a nucleotide sequence encoding RV structural proteins C, E2 and E1; and b) an expression vector comprising a RV fusion gene linked in translation frame to a promoter, wherein the RV fusion gene comprises: i) a first nucleotide sequence encoding a RV that is devoid of E1 gene; and ii) a second nucleotide sequence, linked in translation frame to the first nucleotide sequence, encoding a humoral immunogenic viral protein; wherein the expression vector is devoid of RV E1 protein-encoding nucleotide sequence.

Yet in another aspect, the invention relates to an isolated expression vector comprising a RV fusion gene linked in translation frame to a promoter, in which the RV fusion gene comprises: i) a first nucleotide sequence encoding a RV that is devoid of E1 gene; and ii) a second nucleotide sequence, linked in translation frame to the first nucleotide sequence, encoding a humoral immunogenic viral protein, in which the expression vector is devoid of RV E1 protein-encoding nucleotide sequence. The isolated expression vector may further comprise a third nucleotide sequence, which links in translation frame to the first or the second nucleotide sequence and encodes HN of hPIV-3. In one embodiment of the invention, the humoral immunogenic viral protein is selected from the group consisting of RSV F protein and HN protein of hPIV-3.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Materials and Methods

Cells and viruses. Vero cells, baby-hamster kidney 21 (BHK 21) cells, Human embryonic kidney cells (2937), and human larynx carcinoma cells (HEp-2) (ATCC® CCL 23) were grown and maintained in DMEM medium (HYCLO-NET™) supplemented with 10% fetal bovine serum (FBS, Biological), and 1% penicillin/streptomycin (Biological) in an incubator maintained at 37° C. and equilibrated with 5% $CO_2$.

Culture of respiratory syncytial virus. Human RSV B1 strain was purchased from American Type Culture Collection (ATCC®) and propagated in HEp-2 cells by inoculating an MOI (multiplicity of infection) of 0.2 RSV-B1 to $1 \times 10^7$ HEp-2 cells. Infection was allowed to take place for 4 days before the infected cells were harvested by scraping, collected in a centrifuge tube and pelleted by centrifugation for 5 min at 3000 rpm. The cell pellets were broken up with a tissue grinder to release virions, cell debris was removed by centrifugation for 10 min at 3000 rpm. Purification of viruses was performed by centrifugation of the culture supernatant through a 15% sucrose (in PBS, pH 7.2) gradient for 2 hours at 30,000 rpm. The virus collected was resuspended in PBS, pH 7.2.

The titer of RSV was determined by a standard plaque assay (Crowe et al., (1994) "A further attenuated derivative of a cold-passaged temperature-sensitive mutant of human respiratory syncytial virus retains immunogenicity and protective efficacy against wild-type challenge in seronegative chimpanzees" *Vaccine* 12(9): 783-90). Briefly, 100 µL of various dilutions of purified virus preparations were individually added to $5 \times 10^5$ HEp-2 cells cultured in a 12-well plate (Corning). Each of the cultures was overlaid with DMEM containing 1.5% methylcellulose (Sigma-Aldrich) and incubated for 5 to 6 days for plaques to develop, followed by staining with hematoxylin and eosin. The number of plaques was counted under a light microscope. The concentration of viral particles was expressed as plaque forming units per ml (PFU/mL).

Construction of In-Frame Bivalent Vaccinal Virus Recombinants

To construct a bivalent vaccine for RV and RSV, an RV expression vector was employed. The vector M33 of RV was used to first construct an expression vector for RV genes. The RV E1 gene was then replaced with the RSV fusion (F) protein gene to construct an in-frame bivalent vaccinal virus recombinant that expresses both RV and RSV F genes. The nucleotide sequence of M33 rubella virus complete genome (9759 bp) is listed as SEQ ID NO: 15, in which C protein is from nt. 6509 to nt. 7408; E2 protein is from nt. 7409 to nt. 8254; E1 protein is from nt. 8255 to nt. 9697.

Immunization of Mice

BALB/c mice were anesthetized with isoflurane and primed with $1 \times 10^4$ pfu/50 µL of ΔE1 RV-RSV-F0, or wild type RVwt via the subcutaneously (s.c.) route. Twenty days later, animals were boosted s.c. with the same dose of the respective immunogens. Mice were bled 10 days after booster immunization, antiserum samples that contained anti RSV F protein antibody were individually analyzed against heat inactivated RSV-B1 (HIRSV-B1) or heat inactivated RV (HIRV) in ELISA. The membrane surface of the HIRSV-B1 viral particle contains F protein, which can be utilized to recognize the anti-RSV F antiserum. HIRSV-B1 and HIRV were prepared from purified RSV B1 or RV viruses treated with heat shock at 80° C. water bath for 1 hr, then aliquoted and stored at −80° C. freezer. Viruses lost infectious activity after the heat shock, as confirmed by plaque assay.

ELISA

Blood samples were collected by tail vein puncture of mice 10 days after the booster immunization. After forming blood clots at room temperature, the blood samples were centrifuged at 12,000 rpm for 20 min to collect sera, followed by inactivation at 56° C. for 30 min. ELISA was performed to detect RSV-specific IgG and RV-specific IgG antibodies. Briefly, 96-well Immulon 2B plates (Corning) were coated with $2.5 \times 10^3$ pfu of heat-inactivated (80° C. for 1 hr) RSV-B1 virus (HIRSV-B1) or heat-inactivated rubella (HIRV) in 100 uL of sterile sodium carbonate buffer (8.4 g/L $NaHCO_3$, 3.5 g/L $Na_2CO_3$, pH 9.5) at 37° C. overnight. The antigen-coated ELISA wells were then blocked with 5% skim milk in PBS at room temperature for 1 hour, and washed three times with 200 µL of PBS containing 0.05% Tween 20. Individual sera were 2-times serially diluted (20 to 1280) and 100 uL were added to virus-coated well for 2 hours at room temperature. The reaction was allowed to take place at room temperature for 2 hours. Wells were washed three times with 200 µL of wash buffer (PBS containing 0.5% TWEEN® 20). One hundred µL of horseradish peroxidase (HRP)-conjugated donkey anti-mouse IgG antibodies (Jackson) were added to detect the binding of anti-RSV or anti-RV antibodies. After one hour incubation at room temperature, the plates were washed four times with the wash buffer, and 70.0 µL of SureBlue™ TMB peroxidase substrate solution (Kirkegaard & Perry Laboratories) were added to the wells. Following 15 min incubation in the dark, absorbance at wavelength 450 nm was recorded using an ELISA reader (SPECTRA NAX M2, Molecular Devices).

I. Construction of Vectors Expressing RV Genes, Propagation and DNA Sequence Determination Plasmid pRVwt. A plasmid containing cDNA encoding the genome of the RV vaccine strains, RA 27/3 was purchased from ATCC®. The plasmid was amplified in DH5α cells. The full-length RV27/3 cDNA was subcloned into the vector pcDNA3.1 (Nitrogen) at Cori/Hindi sites under the control of the cytomegalovirus enhancer element/promoter CMV-P to obtain the plasmid pRVwt (FIG. 1A). The term "NS" stands for nonstructural protein, and the term "SP" stands for structural protein. "ORF" stands for open reading frame." "UTR" sands for untranslated region, i.e., regions of mature RNA that do not code for proteins. The term "C" stands for the nucleotide sequence of the rubella virus capsid protein (C) gene. The terms "E1" and "E2" stand for rubella virus E1 and E2 proteins.

Plasmid pΔE1RV. To generate pΔE1RV, the E1 glycoprotein-encoding sequence located at the SP-ORF region of the RV cDNA in the expression vector pRVwt was removed by digestion with the restriction enzymes Bali/Hindi and relegating the ends with T4 DNA polymerase/lipase. The resultant replica vector pΔE1RV retained the entire NS-ORF and the C-E2 domains of the SP-ORF region. The DNA sequences of all the gene inserts in the plasmids were confirmed by DNA sequencing. The nucleotide sequence of RSV F0 is listed as SEQ ID NO: 13, in which the sequence encoding a signal peptide is from nt. 25 to nt. 93; the sequence encoding F2 is from nt. 94 to nt. 501; the sequence encoding F1 is from nt. 502 to nt. 1665; the sequence encoding TM is from nt. 1666 to nt. 1830.

Plasmid pΔE1RV-GFP. To monitor expression of the RV gene insert in the pseudo (E1-deleted) virus assembly, the human green fluorescence protein GFP gene was synthesized by PCR using the plasmid pEGFP-C1 (Clontech) as a template and inserted into the 3' end of the E2 domain as a reporter gene (FIG. 1C). The plasmid pΔE1RV-GFP was transfected into the competent, stable packaging cell line BHK 21 cells. The stable transformed cell line BHK-C-E2-E1 was a transfectant with full-length RV cDNA.

II. Construction of Bivalent Vectors Expressing RV and RSV F Genes

Plasmids pΔE1RV-Inserts. Human RSV fusion (F) protein expression vectors were constructed using the plasmid pΔE1RV. The plasmids pΔE1RV-GFP, pΔE1RV-RSV-$F_0$, and pΔE1RV-RSV-F$_0$ΔTM were generated by inserting green fluorescence protein (GFP)-encoding cDNA, codon-optimized synthetic RSV full-length F cDNA (F$_0$), and transmembrane domain-deleted F cDNA (F$_0$ΔTM) at the 3' end of the E2 domain of pΔE1RV. The term "TM" represents transmembrane domain.

Construction of viral packaging cell lines. The pRV-C-E2-E1-transfected BHK cells, designated BHK-C-E2-E1, was obtained as a gift from Fr Gillam, which produce C, E2 and E1 proteins. Vero-C-E2-E1 packaging cell line was constructed as follows. First, the plasmid pRV-C-E2-E1 was generated. A cDNA encoding all three structural proteins C-E2-E1 of RV was synthesized by PCR amplification of the entire SP-ORF region of the plasmid pRVwt. The C-E2-E1 cDNA was inserted into the vector pcDNA3.1, which contains a CMV promoter, at the multiple cloning sites Cori and Hindi to generate the plasmid pRV-C-E2-E1 (which does not contain RV NS-ORF). The DNA sequences of the gene insert in the plasmid pRV-C-E2-E1 was confirmed by DNA sequencing. The plasmid pRV-C-E2-E1 was transfected into Vero cells to make Vero-C-E2-E1 packaging cell line. Transfectants were cultured in the presence of neomycin antibiotics (G418, Sigma-Aldrich) for 14-21 days until the antibiotic-resistant cell clones were produced. A vaccine is then prepared from an RV expression vector co-expressing transfected Vera cells using any technique known to the art for such preparation.

Plaque formation assay. The titer of RV was determined by a standard plaque assay [39]. Briefly, 100 µL of various dilutions of purified virus preparations were individually added to 5×10$^5$ BHK. 21 cells cultured in a 12-well plate (Corning). Each of the cultures was overlaid with DMEM containing 1.5% methylcellulose (Sigma-Aldrich) and incubated for 10 days for plaques to develop, followed by staining with hematoxylin and eosin. The number of plaques was counted under a light microscope. The concentration of viral particles was expressed as plaque forming units per ml (PFU/mL).

Reverse transcriptase-PCR(RT-PCR). Recombinant transcripts were analyzed by RT-PCR. Total RNA were extracted from pRVwt-infected Vero and 293 T cells. Briefly, BHK and Vero or 293T cells transfectants were grown with the antibiotic selection, collected, and lysed for total RNA isolation. RNA samples were isolated with TRIZOL reagent (Life Technologies, Inc., Gaithersburg, Md.) following the manufacturer's instructions. Purity of isolated RNA was evaluated spectrophotometrically by the A260/A280 absorbance ratio. Two micrograms of total RNA were used for a reverse transcription polymerase chain reaction (RT-PCR) to amplify mRNA of target gene by adding corresponding pairs of specific primers into the mixture of one-step RT-PCR Premix reagent (iNtRON Biotechnology, Inc.). Program of RT-PCR reaction was set at 45° C. for 30 min, 94° C. for 5 min followed by 35 cycles of 94° C. for 1 min, anneal temperature of 60° C. for 1 min and 72° C. for 1 min followed by incubation at 72° C. for 7 min for amplification of E1 gene. To detect the expression of RV E2, NS genes, and the inserted genes GFP and RSV F, RT-PCR was performed using specific primer pairs for E2, NS, GFP, and RSV F at the anneal temperature of 55° C., 62° C., 60° C., and 58° C. for 1 min, respectively.

Transfection and fluorescent microscopic analysis of cell cultures. The fluorescence emitted from the plasmid pΔE1 RV-GFP infected BHK-21 cells was vision-detected under the UV-fluorescence microscope after 24 and 48 hours of transfection.

Analysis of proteins made in recombinant-transfected cells. Lysates were subjected to SDS-PAGE electrophoresis and western blot analysis using commercially available antibodies specific to C, E2, and E1 proteins of RV.

Construction of in-frame bivalent vaccinal virus recombinants. Human respiratory syncytial virus fusion (F) protein were expressed as a bivalent vaccinal virus vectors. The plasmids pΔE1RV-RSV-GFP, pΔE1RV-RSV-F$_0$, and pΔE1RV-RSV-F$_0$ΔTM were generated by inserting green fluorescence protein (GFP) cDNA, codon-optimized synthetic RSV full length F cDNA (F$_0$), and transmembrane domain-deleted F cDNA (F$_0$ΔTM) at the 3' end of the E2 domain of pΔE1RV. The individual replicons obtained were transfected into BHK-C-E2-E1 and Vero-C-E2-E1 packaging cell lines. The respective viral gene expression is determined by RT-PCR with primer pairs specific to the inserted GFP and RSV F gene. Pseudo-virions produced from the transfectants were analyzed by UV-fluorescence microscopy for GFP expression or western blotting using commercially available antibodies to RSV F.

Animals and generation of anti-RSV F sera. Six to eight week old female BALB/c mice were purchased from the National Laboratory Animal center, Taiwan. Mice were kept and maintained in pathogen-free cages at the Animal Care Center of the National Health Research Institutes, Zhunan Campus, throughout the animal study. Mouse polyclonal anti-RSV F sera were collected at day-20 from BALB/c mice intranasally immunized with live RSV on day-0 and day-10.

SDS-PAGE gel Analysis and Western Blotting. Cell pellets were lysed to release the intracellular proteins for immunoblot analysis. The lysis was performed by treating cell pellets with pH 8.0 lysis buffer (containing 50 mM Tris-HCl, 150 mM NaCl, 1% Triton X-100, and 1× protease inhibitor cocktail (Roche). Lysis was allowed to take place on ice for 30 minutes with occasional pipetting. Cell debris was removed by centrifugation at 14,000×g for 20 minutes at 4° C. The cell lysate was subjected to SDS-PAGE electrophoresis and proteins were transferred onto a Hybond ECL nitrocellular membrane (Amersham).

The membrane was blocked with 5% skim milk in Tris-buffer saline, pH 7.2, at room temperature for 1 hour, washed twice with PBS containing 0.05% Tween 20 (PBST) and incubated with a polyclonal mouse antiserum raised against RSV at 4° C. overnight. The membrane was washed twice with PBST, and anti-mouse HRP-conjugated antibody (KPL Immunochemical) diluted at 1:5000 in PBS containing 5% skim milk was then added to the membrane for protein visualization. After 1 hour incubation at room temperature, the membrane was washed twice with PBST before it was treated with SuperSignal West Pico chemiluminescent substrate (Pierce) and exposed onto an X-ray film.

Construction of in-frame polyvalent vaccinal virus recombinants. Construction of the expression vector containing the HN gene of hPIV-3 is preformed as follows. A cDNA encoding HN is synthesized by RT-PCR from the total mRNA extracted from the C243 strain of hPIV-3 (VR-93, American Type Culture Collection (ATCC®), Rockland, Md.) infected LLC-MK-2 cells (ATCC® CCL 7.1). A trivalent candidate vaccine designated as pΔE1R-hPIV-3 HN-RSV-F$_0$ (FIG. 1E) is made as follows. The hPIV-3-HN cDNA fragment is subcloned into a multiple cloning site of pcDNA3.1 to generate the plasmid pcDNA3.1-hPIV-3 HN. The RSV-F$_0$ cDNA fragment is inserted into the 3' end of HN gene to obtain the plasmid pcDNA3.1-hPIV-3 HN-RSV-F$_0$. The composite hPIV-3 HN-RSV-F$_0$ fusion gene is excised from the plasmid pcDNA3.1-hPIV-3 HN-RSV-F$_0$ and inserted into the 3' end of the E2 domain of pΔE1RV to generate the polyvalent expression vector pΔE1RV-hPIV-3-HN-RSV-F$_0$. The sequence encoding HN of hPIV-3 is listed as SEQ ID NO: 14.

Results

Generation of Rubella Virus Vaccinal Strain Expression Vector Containing Human Respiratory Syncytial Virus Fusion Protein Gene FIGS. 1A-1G show the structural maps of the individual plasmids. FIG. 1A is a schematic representation of an infectious wild-type rubella virus (RV) gene construct containing a full-length RV cDNA. The 5'-terminal region of the nonstructural protein open reading frame (NS-ORF) and the 3'-terminal region of the structural protein open reading frame (SP-ORF) are shown as boxes, and the junction UTR is shown as a line. The plasmid pRVwt (FIG. 1A) was generated by inserting an RV cDNA clone obtained from Dr Gillam (University of British Columbia, Canada) into a pcDNA3.1 vector (Nitrogen). The plasmid pRVwt was further modified to delete the E1 gene to construct the plasmid pΔE1RV (FIG. 1B). To track the replica nature of the plasmid pΔE1RV, green fluorescence protein (GFP) reporter gene was inserted to generate the expression vector pΔE1RV-GFP (FIG. 1C). Finally, the plasmids pΔE1RV-RSVF$_0$ and pΔE1RV-RSVF$_0$ΔTM, which contain the RSV F$_0$ (full length) and RSV F$_0$ΔTM (transmembrane fragment truncated) genes, were constructed (FIGS. 1D-1E).

the infectivity of the virus particles produced from Vero cells, the cell culture supernatant and homogenized cell pellet of pRVwt-infected Vero cells were used to infect BHK-21 cells. Plaque assay was performed by incubating BHK 21 cells with 2-fold serial dilutions of Vero cell pellet extract (P), culture supernatant (S) of pRTwt-infected Vero cells (FIG. 2A), or non-infected Vero cell culture medium (NP). A solution of DMEM containing 1.5 percent methylcellulose was added to each plate to overlay the virus and cell culture plate. After 10 days of incubation, the virus plaques, irrespective of size, were counted after staining the surrounding cell areas with hematoxylin and eosin. Virus plaques were seen in those areas where the virus infected and reproduced in the cells (FIG. 2A).

In the pRVwt-infected Vero cells, infectious RV were both detected in the homogenized cell pellets (FIG. 2A, left panel) and culture supernatant (FIG. 2A, right panel). Approximately $10^4$ PFU/mL of RV particles were obtained by infecting $1\times10^6$ Vero cells with 5.0 μg of pRVwt, and that was 1 $\log_{10}$ higher than what were reported in the literature (Liang et al., (2001) "Rubella virus RNA replication is cis-preferential and synthesis of negative- and positive-strand RNAs is regulated by the processing of nonstructural protein" *Virology* 282(2): 307-19).

TABLE 1*

| Target gene | Forward primer | SEQ ID NO. | Reverse primer | SEQ ID NO. |
|---|---|---|---|---|
| RV E1 | aggctttcacctacctctgc | 1 | cgccagggttgaagtaaga | 2 |
| RV E2 | cgccagggttgaagtaaga | 3 | atagcgcagccaaaccgggt | 4 |
| RV C | gcttctactaccccatcaccatgg | 5 | taaaagaccgcgccttcgcc | 6 |
| RV NS | atggagagactcctagatgaggtt | 7 | acatctgcatgggtgtgtagtag | 8 |
| RSV F | tggagctgcccatcctgaag | 9 | tggactgcatcagcagctgc | 10 |
| GFP | tgagcaagggcgaggagctgtt | 11 | aagatggtgcgctcctggacgtag | 12 |

*All primers are listed 5' to 3'.

The wild-type RV 27/3 replica delivery vector pRVwt contains a nonstructural open reading frame (NS-ORF) and a structural open reading frame (SP-ORF) (FIG. 1A). The SP-ORF includes C, E2, and E1 regions.

FIG. 1B shows the E1 defective RV replica delivery vectors pΔE1RV, which is deleted of the E1 from the pRVwt. The expression vector pΔE1RV contains E1 envelope protein-deleted RV cDNA. It retains the expression of RV viral nonstructural (NS) and structural proteins C and E2, and retains virus-packaging function in packaging cell lines such as Vero cells or BHK-21 cells. Moreover, E1-deletion permits insertion of a foreign gene into the plasmid pΔE1RV.

FIG. 1C shows the plasmid pΔE1RV-GFP, a modification from pΔE1RV to incorporate the GFP reporter gene. The replica delivery vectors pΔE1RV-RSVF$_0$ and pΔE1RV-RSVF$_0$ΔTM contain the full length RSV F (F$_0$) and the transmembrane domain truncated RSV F (F$_0$ΔTM) genes, respectively.

Vero Cells as a Host for RV Gene Expression and Viral Productions

Figure 2B:
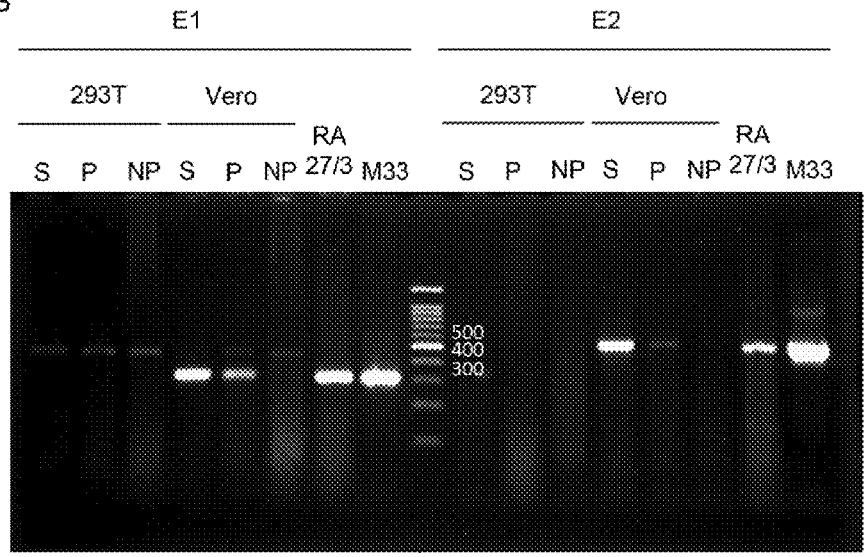
FIG. 2B is a photograph of gel electrophoresis analysis of RT-PCR products.

Two cell lines, Vero and 293T cells, were tested for whether they could efficiently express recombinant RV structural proteins (Capsid, E2 and E1 protein) for production of recombinant RVwt. The results showed that Vero cells, but not 293T cells, permitted the pRVwt replica expression of RV genes and led to the production of infectious virus particles. To test FIG. 2B shows the result of RT-PCR analysis. The E1 and E2 mRNA were detected in the pRVwt-infected Vero but not 293T cells (FIG. 2B). The viral E1 and E2 mRNA were reverse transcribed and the reverse transcript amplified by PCR using primer pairs specific to E1 and E2 gene. The bands detected at 300K and 500K corresponded to RV E1 and E2 mRNA. Plasmids RV 27/3 and RV M33 DNAs were used as positive controls in the PCR reaction using primers pairs specific to E1 or E2 genes. Table 1 lists the sequences of primer pairs used in the RT-PCR analysis.

Expression of Recombinant Genes GFP and RSV F from the E1-Deleted RV Expression Vectors Whether the deletion of the E1 gene from the plasmid pRVwt would affect the expression of the rest of RV gene inserts in host cells was investigated using a reporter gene construct. In general, BHK-21 cells were transfected with respective expression vectors and the mRNA expression was assayed by RT-PCR analysis.

The expression of E1-deleted expression vector pΔE1RV was assayed by detecting the GFP protein production (e.g., GFP fluorescence activity) and GFP mRNA expression in the pΔE1RV-GFP plasmid-transfected-BHK 21 cells. The fluorescent GFP was observed in the pΔE1RV-GFP-transfected BHK-21 cells at 24 hrs and 48 hrs after the transfection, but not in the pΔE1 RV or mock (pcDNA3.1) transfected BHK-21 cells.

Figure 3A:
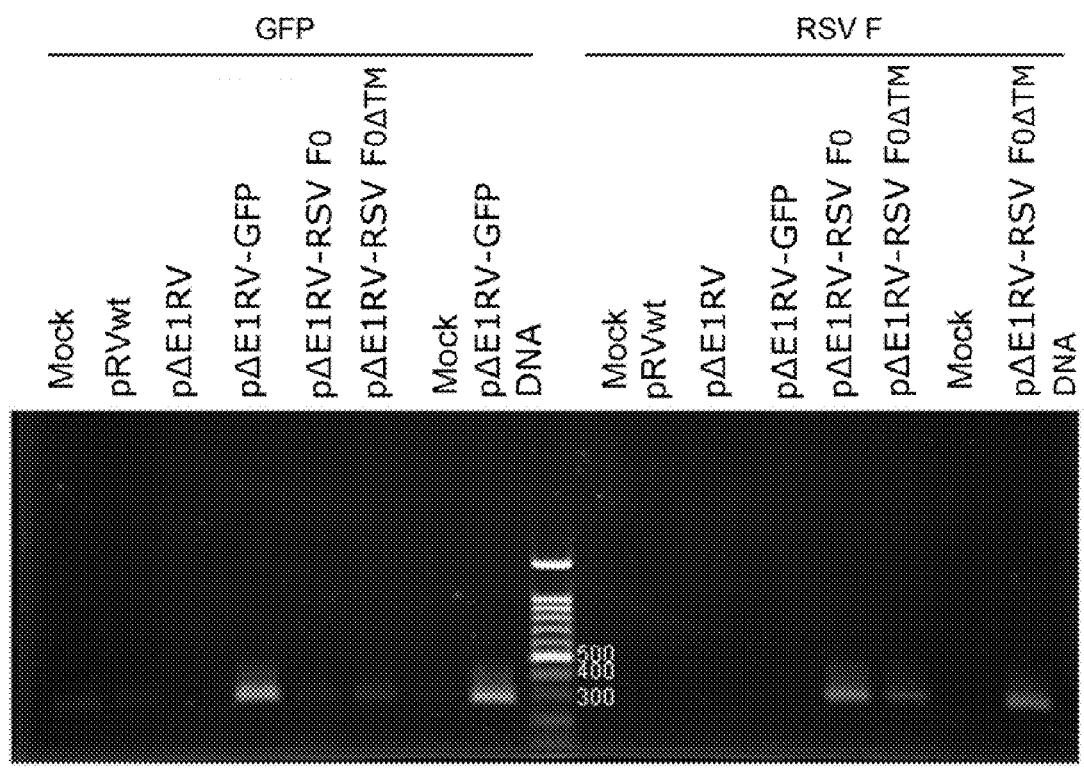
FIG. 3A is a photograph of gel electrophoresis analysis of RT-PCR products.

The E1-deleted RV expression vector was functional in transfected BHK-21 cells. The transfectants showed expression of the inserted RV, GFP and RSV F genes, but not the RV E1 gene. As shown in FIG. 3A, the RT-PCR analysis performed on the total RNA extracted from the pΔE1 RV-GFP-transfected BHK-21 cells using a primer pair specific to the GFP gene detected a DNA band at a size of about 295 bp, indicating GFP mRNA expression in the pΔE1RV-GFP transfected-BHK 21 cells.

The RT-PCR analysis performed on the total RNA extract from the pΔE1RV-RSVF$_0$ and pΔE1RV-RSVF$_0$ΔTM transfected BHK-21 cells using a primer pair specific to the region between 326-631 bps of the RSV F gene detected DNA bands at a size of about 305 bp, which corresponded to the gene insert RSV F$_0$ or RSV F$_0$ΔTM (FIG. 3A).

Figure 3B:
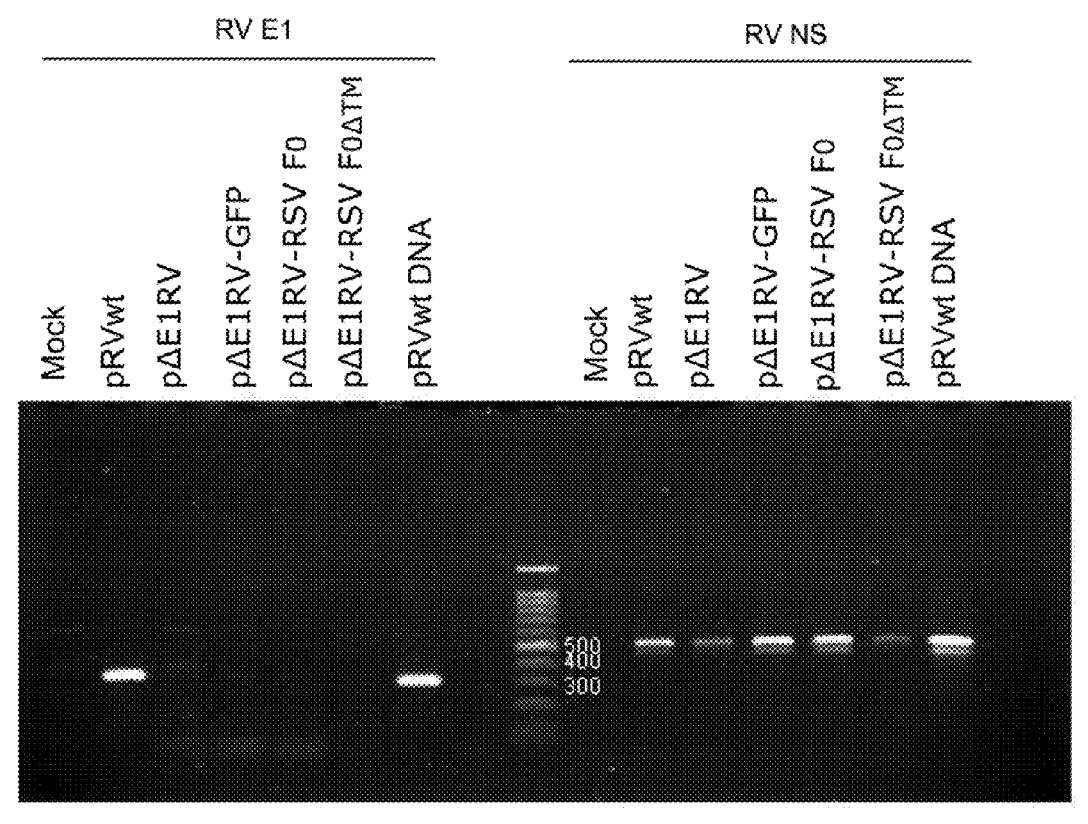

The RT-PCR analysis on the RNA extract from E1-protein-deleted RV expression vector transfectants using a primer pair specific to RV E1 structural gene did not detect E1 expression (FIG. 3B), while the wild-type plasmid pRVwt-transfected cells showed the expression of E1 mRNA at 312 bp. Using a primer pair specific to nonstructural protein (NS) gene, a band of 532 bp was detected for the nonstructural protein (NS) gene expression in all the transfectants' RNA extract except the mock transfectant (FIG. 3B). The plasmid pRVwt DNA was used as a positive control.

Expression of RSV F Protein from Bivalent Vaccinal Virus Vector

Figure 4:
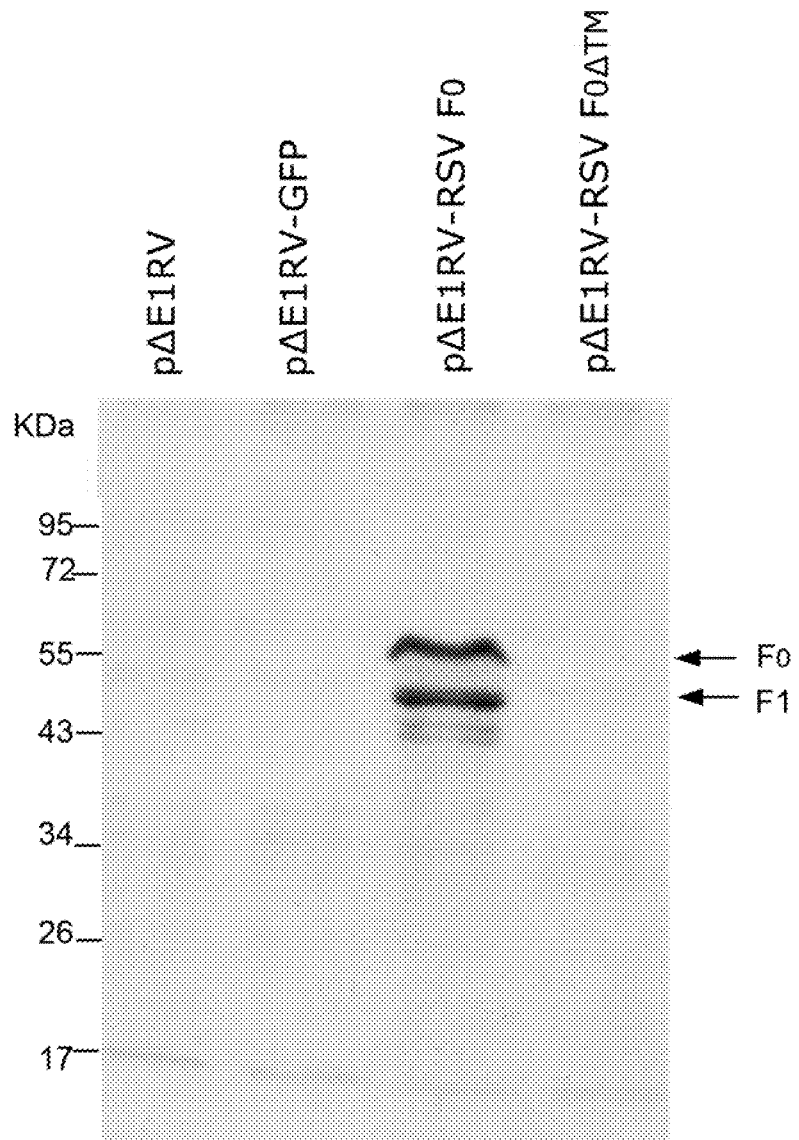
FIG. 4 is a photograph of SDS-PAGE gel electrophoresis of the protein samples from BHK-21 transfectant whole cell lysates.

The cell lysate from the E1-deleted RV expression vector-transfected BHK-21 cells was immunoblotted with mouse polyclonal anti-RSV F sera. As shown in FIG. 4, the proteins F$_0$ and F$_1$ were detected in the lysate of the pΔE1RV-RSV F$_0$ transfected cells at the bands of about 62 KDa and 49 Kda, respectively. In the lysate of the pΔE1RV-RSV F$_0$ΔTM transfected cells, however, the F protein was not detected (FIG. 4), which indicated that the deletion of TM domain from F protein might have lead to no or low F protein expression in the transfected cells.

Two packaging cell lines, BHK-C-E2-E1 and Vero-C-E2-E1, were tested for production of defective RV. BHK cells have been shown to express exceptionally high yield of RV structural proteins. Vero cells have been established as a host for clinical production of viral vaccines. The production of bivalent expression vector was tested in BHK-C-E2-E1 and Vero-C-E2-E1 cells. The BHK-C-E2-E1 is a stable cell line transfected with pRV-C-E2-E1 and constitutively expresses RV capsid, E2 and E1 structural proteins. The Vero-C-E2-E1 cell line is a stable cell line transfected with pRV-C-E2-E1, which also constitutively expresses RV capsid, E2, and E1 structural proteins.

The E1 protein-deleted expression vectors pΔE1RV-RSV-F$_0$ and pΔE1 RV-RSV-F$_0$ΔTM were generated by inserting codon-optimized synthetic RSV full-length F cDNA (F$_0$) and transmembrane domain-deleted F cDNA (F$_0$ΔTM) at the 3' end of the E2 domain of pΔE1RV. The E1 gene deletion rendered the RV defective because the whole virus particles could not be produced due to the lack of E1 protein. The E1 deletion, however, did not affect the viral packaging of viral genes with capsid protein. Thus, the expression vector pΔE1-RV could infect a host only one time.

The individual replicons, pΔE1RV, pΔE1RV-GFP, pΔE1RV-RSV-F$_0$ and pΔE1RV-RSV-F0ΔTM, were transfected into the BHK-C-E2-E1 and Vero-C-E2-E1 packaging cell lines. The packaging cell line can make E1 protein needed for the defective RV to form a whole viral particle. It was found that the viral yield of E1-deleted RV in BHK-C-E2-E1 was low. Vero-C-E2-E1 cells were better than BHK-C-E2-E1 for production of the defective RV. The cell line Vero-C-E2-E1 was thus chosen to produce pseudo RV (E1 gene deleted, replication defective) for the production of regulatory-approvable batches of RV plus RSV bivalent vaccine candidates.

Figure 5:
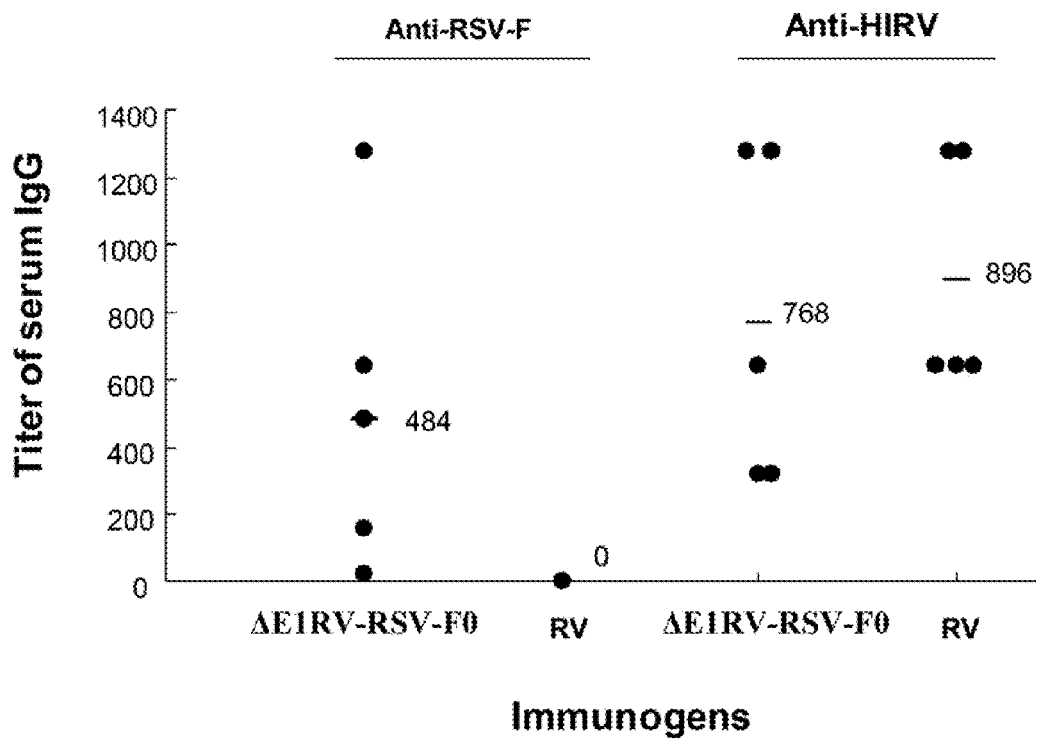

Bivalent Chimeric Viral Vaccine ΔE1-RV-RSV-F0 Elicited RSV and RV Specific Humoral Response in Mice FIG. 5 shows cross-reactivity of immune sera raised against ΔE1RV-RSV-F and RV, respectively. Serum samples were collected from individual BABL/c mice administered twice via s.c. route with $10^4$ pfu of ΔE1RV-RSV-F0 or wild type RV. Sera collected 10 days after the booster administration were assayed against heat-inactivated RSV-B1 (HIRSV-B1) or heat-inactivated RV (HIRV) immobilized on ELISA plate wells. Results obtained were shown as IgG titers for individual sera corresponding to mean titers for each experimental group. Each dot in FIG. 5 represents serum antibody titer of a mouse. The bar (—) represents a mean titer from each experimental group. Five mice were used for each experimental group.

As shown in FIG. 5, anti-HIRSV-B1 antibodies were detected in the sera of ΔE1-RV-RSV-F0 immunized mice, but not in the sera of RV-immunized mice. The virus binding titers in the sera from ΔE1-RV-RSV-F0-immunized mice were in the range of 20 and 1280 (mean=484). Immune sera raised against HIRV were detected in both ΔE1-RV-RSV-F0 and RV-immunized groups with mean binding titers of 768 and 896, respectively. The results indicated that the bivalent chimeric ΔE1-RV-RSV-F0 vaccine was able to induce both anti-RSV and anti-RV humoral immunity in the mouse model.

Expression of hPIV3 HN Protein from Polyvalent Vaccinal Virus Vector

Hemaagglutinin-neuramindase (HN) of human Parainfluenza Virus Type 3 (hPIV-3) is a 70 KDa glycoprotein that binds to membrane-bound sialic acid-containing glycoprotein to mediate the attachment and subsequent fusion of the virus to the target cell. HN has been shown to contain antigenic sites that induce PIV-3-specific protective neutralizing antibodies in animal and in human. FIGS. 1F and 1G show the expression vectors pΔE1RV-hPIV-3 HN-RSV F$_0$ and pΔE1RV-hPIV-3 HN. The HN gene may be fused with either the RSV F$_0$ gene to form hPIV-3 HN-RSV-F$_0$ (FIG. 1F) or RSV-F-hPIV3 HN (map not shown) fusion gene.

The invention relates to a regulatory authority approved vaccine strain expression vector RV27/3 and M33 that are deleted of the E1 gene. The RV-specific protective humoral response is thus mainly confined to those generated against the C protein. A combination of mucosal-subcutaneous immunization regimen to compare mucosal delivery may be performed to establish the criteria needed for the recombinant RV27/3 and M33 vaccine candidate to induce optimized effector immune responses against RSV and RV.

The polyvalent vaccines, ΔE1RV-hPIV-3 HN-RSV F$_0$ and ΔE1 RV-hPIV-3 HN, can afford a specific immunity against hPIV3 infections in addition to immune responses against RV and RSV infections. Previous studies showed that a chimeric human-bovine parainfluenza virus type 3 expressing measles vines hemagglutinin, although being attenuated for replication, was immunogenic in rhesus monkeys (MARIO H. SKIADOPOULOS, et al., JOURNAL OF VIROLOGY, November 2001, p. 10498-10504). Infectious replication-defective HIV-1 particles pseudotyped with hemagglutinin-neuraminidase (HN) and fusion (F) proteins derived from human parainfluenza virus type 3 (HPIV3) have also been reported. These HIV-1 (HPIV3) pseudotype vectors may have unique properties that will make them useful for efficient gene transfer into a variety of human tissues. (Grzybowski, B.

et al., Engineering in Medicine and Biology, 2002. 24th Annual Conference and the Annual Fall Meeting of the Biomedical Engineering Society] EMBS/BMES Conference, 2002. Proceedings of the Second Joint).

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A chimeric viral particle whose genome comprises:
   a) a first nucleotide sequence encoding rubella virus (RV) proteins, wherein the proteins encoded by the first nucleotide sequence are devoid of RV E1 protein; and
   b) a second nucleotide sequence, linked in translation frame to the first nucleotide sequence, encoding respiratory syncytial virus (RSV) F protein;
   wherein the chimeric viral particle is free of RV E1 protein-encoding gene.

2. The chimeric viral particle of claim 1, further comprising:
   c) a third nucleotide sequence, linked in translation frame to the first or the second nucleotide sequence, encoding hemagglutinin-neuramindase (HN) of human Parainfluenza Virus Type 3 (hPIV-3).

3. The chimeric viral particle of claim 1, wherein the first nucleotide sequence comprises:
   i) a first polynucleotide sequence encoding RV nonstructural proteins;
   ii) a second polynucleotide sequence encoding RV capsid (C) protein; and
   iii) a third polynucleotide sequence encoding RV E2 protein.

4. A viral vaccine comprising a nontoxic, physiologically acceptable carrier and an immunogenic amount of the chimeric viral particle of claim 1.

5. A viral vaccine comprising a nontoxic, physiologically acceptable carrier and an immunogenic amount of the chimeric viral particle of claim 2.

6. A virus packaging cell which generates the chimeric viral particle of claim 1, wherein the virus packaging cell's genome comprises:
   a) a nucleotide sequence encoding RV structural proteins C, E2 and E1; and
   b) an expression vector comprising:
      i) a promoter;
      ii) a first nucleotide sequence, linked in translation frame to the promoter, encoding RV proteins, wherein the proteins encoded by the first nucleotide sequence are devoid of RV E1 protein; and
      iii) a second nucleotide sequence, linked in translation frame to the first nucleotide sequence, encoding RSV F protein;
   wherein the expression vector is devoid of RV E1 protein-encoding nucleotide sequence.

7. A virus packaging cell which generates the chimeric viral particle of claim 2, wherein the virus packaging cell's genome comprises:
   a) a nucleotide sequence encoding RV structural proteins C, E2 and E1; and
   b) an expression vector comprising:
      i) a promoter;
      ii) a first nucleotide sequence, linked in translation frame to the promoter, encoding RV proteins, wherein the proteins encoded by the first nucleotide sequence are devoid of E1 protein;
      iii) a second nucleotide sequence, linked in translation frame with the first nucleotide sequence, encoding respiratory syncytial virus (RSV) F protein; and
      iv) a third nucleotide sequence, linked in translation frame to the first or the second nucleotide sequence, encoding hemagglutinin-neuramindase (HN) of human Parainfluenza Virus Type 3 (hPIV-3);
   wherein the expression vector is devoid of RV E1 protein-encoding nucleotide sequence.

8. A method of eliciting a humoral immune response against RV and RSV in a mammal, comprising administering to the mammal the viral vaccine of claim 4, thereby eliciting the humoral immune response against RV and RSV in the mammal.

9. A method of eliciting a humoral immune response against RV, RSV and hPIV-3 in a mammal, comprising administering to the mammal the viral vaccine of claim 5, thereby eliciting the humoral immune response against RV, RSV and hPIV-3 in the mammal.

10. A chimeric viral particle whose genome comprises:
    a) a first nucleotide sequence encoding RV proteins, wherein the proteins encoded by the first nucleotide sequence are devoid of RV E1 protein; and
    b) a second nucleotide sequence, linked in translation frame to the first nucleotide sequence, encoding an immunogenic foreign viral protein;
    wherein the chimeric viral particle is free of RV E1 protein-encoding gene.

11. The chimeric viral particle of claim 10, wherein the second nucleotide sequence, linked in translation frame to the first nucleotide sequence, encodes hemagglutinin-neuramindase (HN) of human Parainfluenza Virus Type 3 ihPIV-3).

12. The chimeric viral particle of claim 11, whose genome further comprises:
    c) a third nucleotide sequence, linked in translation frame to the second nucleotide sequence, encoding RSV F protein.

13. A viral vaccine comprising a nontoxic, physiologically acceptable carrier and an immunogenic amount of the chimeric viral particle of claim 11.

14. A viral vaccine comprising a nontoxic, physiologically acceptable carrier and an immunogenic amount of the chimeric viral particle of claim 12.

15. A virus packaging cell which generates the chimeric viral particle of claim 11, wherein the virus packaging cell's genome comprises:
    a) a nucleotide sequence encoding RV structural proteins C, E2 and E1; and
    b) an expression vector comprising:
       i) a promoter;
       ii) a first nucleotide sequence, linked in translation frame to the promoter, encoding RV proteins, wherein the proteins encoded by the first nucleotide sequence are devoid of E1 protein; and
       iii) a second nucleotide sequence, linked in translation frame to the first nucleotide sequence, encoding hemagglutinin-neuramindase (HN) of human Parainfluenza Virus Type 3 (hPIV-3);
    wherein the expression vector is devoid of RV E1 protein-encoding nucleotide sequence.

16. A virus packaging cell which generates the chimeric viral particle of claim 12, wherein the virus packaging cell's genome comprises:
    a) a nucleotide sequence encoding RV structural proteins C, E2 and E1; and
    b) an expression vector comprising
       i) a promoter;
       ii) a first nucleotide sequence, linked in translation frame to the promoter, encoding RV proteins, wherein the proteins encoded by the first nucleotide sequence are devoid of E1 protein;
       iii) a second nucleotide sequence, linked in translation frame to the first nucleotide sequence, encoding hemagglutinin-neuramindase (HN) of human Parainfluenza Virus Type 3 (hPIV-3); and iv) a third nucleotide sequence, linked in translation frame to the second nucleotide sequence, encoding RSV F protein;

wherein the expression vector is devoid of RV E1 protein-encoding nucleotide sequence.

17. A virus packaging cell which generates the chimeric viral particle of claim 10, wherein the virus packaging cell's genome comprises:

a) a nucleotide sequence encoding RV structural proteins C, E2 and E1; and b) an expression vector comprising:

i) a promoter;

ii) a first nucleotide sequence, linked in translation frame to the promoter, encoding RV proteins, wherein the proteins encoded by the first nucleotide sequence are devoid of E1 protein; and iii) a second nucleotide sequence, linked in translation frame to the first nucleotide sequence, encoding an immunogenic foreign viral protein;

wherein the expression vector is devoid of RV E1 protein-encoding nucleotide sequence.

18. An isolated expression vector comprising:

i) a promoter;

ii) a first nucleotide sequence, linked in translation frame to the promoter, encoding RV proteins, wherein the proteins encoded by the first nucleotide sequence are devoid of E1 protein; and iii) a second nucleotide sequence, linked in translation frame to the first nucleotide sequence, encoding an immunogenic foreign viral protein;

wherein the expression vector is devoid of RV E1 protein-encoding nucleotide sequence.

19. The isolated expression vector of claim 18, wherein immunogenic foreign viral protein is selected from the group consisting of RSV F protein and HN protein of hPIV-3.

20. The isolated expression vector of claim 19, further comprising a third nucleotide sequence, linked in translation frame to the first or the second nucleotide sequence, encoding HN of hPIV-3.

* * * * *